(12) United States Patent
Pulapura et al.

(10) Patent No.: US 10,442,757 B2
(45) Date of Patent: Oct. 15, 2019

(54) SYNTHESIS OF TYROSINE DERIVED DIPHENOL MONOMERS

(71) Applicant: TYRX, Inc., Monmouth Junction, NJ (US)

(72) Inventors: Satish Pulapura, Bridgewater, NJ (US); Fatima Buevich, Highland Park, NJ (US); Xiangji Chen, Plymouth, MN (US); Suping Lyu, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/972,819

(22) Filed: May 7, 2018

(65) Prior Publication Data

US 2018/0354892 A1 Dec. 13, 2018

Related U.S. Application Data

(60) Provisional application No. 62/516,237, filed on Jun. 7, 2017.

(51) Int. Cl.
| | |
|---|---|
| *C07C 231/02* | (2006.01) |
| *C07C 235/34* | (2006.01) |
| *C07C 231/22* | (2006.01) |
| *B01D 9/00* | (2006.01) |
| *B01D 11/04* | (2006.01) |

(52) U.S. Cl.
CPC .......... *C07C 231/02* (2013.01); *C07C 231/22* (2013.01); *C07C 235/34* (2013.01); *B01D 9/005* (2013.01); *B01D 9/0018* (2013.01); *B01D 9/0036* (2013.01); *B01D 9/0054* (2013.01); *B01D 11/0492* (2013.01)

(58) Field of Classification Search
None
See application file for complete search history.

(56) References Cited

U.S. PATENT DOCUMENTS 8,907,043 B2* 12/2014 James .................... A61L 17/10
435/397

FOREIGN PATENT DOCUMENTS

| WO | 9630331 | 10/1996 |
| WO | 9952962 | 10/1999 |

OTHER PUBLICATIONS

PCT/US2018/031575 International Search Report and Written Opinion of the International Searching Authority dated Jul. 10, 2018 from European Patent Office.

* cited by examiner

*Primary Examiner* — Ana Z Muresan
(74) *Attorney, Agent, or Firm* — Sorell, Lenna & Schmidt, LLP

(57) ABSTRACT

A method for preparing diphenol compounds includes adding a hydroxyphenyl carboxylic acid, a tyrosine ethyl ester, hydroxybenzotriazole hydrate and a solvent and stirring to produce a first solution. EDCI HCl is added to the first solution to produce a first mixture. Ethyl acetate is added to the first mixture to produce a second mixture. The second mixture is added to sodium chloride to produce a third mixture having layer separation. An aqueous layer is removed from the third mixture. The third mixture is extracted with reagents after the aqueous layer has been removed from the third mixture to produce a fourth mixture. Magnesium sulfate is added to the fourth mixture to produce a fifth mixture. The fifth mixture is filtered to produce filtrate. The filtrate is concentrated. Crystallization of the concentrated filtrate is induced. Methylene chloride is added to the crystallized filtrate to produce a solid product.

20 Claims, No Drawings

SYNTHESIS OF TYROSINE DERIVED DIPHENOL MONOMERS

TECHNICAL FIELD

The present disclosure generally relates to methods by which tyrosine derived diphenol monomers are synthesized with significantly improved yield and purity.

BACKGROUND

Conventional methods to synthesize tyrosine derived diphenol monomers are often very time consuming and often result in low yield and/or purity. This disclosure describes an improvement over these prior art technologies.

SUMMARY

In one embodiment, in accordance with the principles of the present disclosure, a method is provided for preparing a tyrosine ethyl ester having the formula:

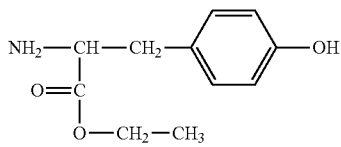

The method comprises dissolving a tyrosine ethyl ester hydrochloride having the formula:

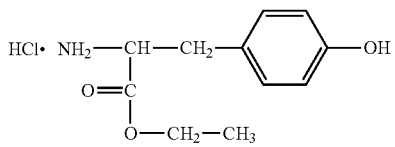

in distilled water to form a solution. The solution is mixed with methylene chloride to form a first mixture. Potassium carbonate is added to the first mixture to form a second mixture comprising separated layers. One of the separated layers is drawn off from the second mixture. Magnesium sulfate is added to the separated layer that was drawn off to form a third mixture. The methylene chloride is removed from the third mixture to form a slurry. Hexane is added to the slurry to form a solid. The solid is washed and dried.

In one embodiment, in accordance with the principles of the present disclosure, a method is provided for preparing diphenol compounds having the formula:

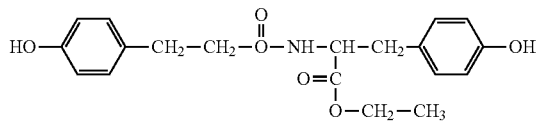

The method includes adding a hydroxyphenyl carboxylic acid having the formula:

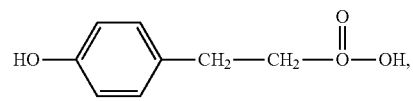

a tyrosine ethyl ester having the formula:

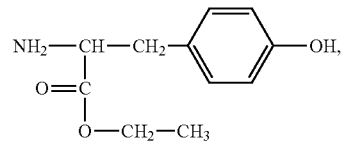

hydroxybenzotriazole hydrate and a solvent to a flask and stirring the contents of the flask to produce a first solution. 3-(Ethyliminomethyleneamino)-N,N-dimethylpropan-1-amine (EDCI) HCl is added to the first solution to produce a first mixture. Ethyl acetate is added to the first mixture to produce a second mixture. The second mixture is added to sodium chloride to produce a third mixture having layer separation. An aqueous layer is removed from the third mixture. The third mixture is extracted with reagents after the aqueous layer has been removed from the third mixture to produce a fourth mixture. Magnesium sulfate is added to the fourth mixture to produce a fifth mixture. The fifth mixture is filtered to produce filtrate. The filtrate is concentrated. Crystallization of the concentrated filtrate is induced. Methylene chloride is added to the crystallized filtrate to produce a solid product.

In some embodiments, the solvent is tetrahydrofuran (THF). In some embodiments, the solvent is a chlorinated solvent. In some embodiments, the first solution comprises at least about 2% excess of the tyrosine ethyl ester relative to the hydroxyphenyl carboxylic acid. In some embodiments, the tyrosine ethyl ester is added to the flask and the hydroxyphenyl carboxylic acid is metered into the flask after the tyrosine ethyl ester is added to the flask. In some embodiments, the first solution, the mixtures, the filtrate and the solid product are maintained at about 5° C. to about 10° C.

In some embodiments, the method further comprises cooling the flask using an ice water bath and stirring the first solution in the cooled flask for about 20 minutes prior to adding EDCI HCl to the first solution. In some embodiments, the first solution, the mixtures, the filtrate and the solid product are maintained at about 5° C. to about 10° C. In some embodiments, the method is complete after about 1 hour to about 2 hours. In some embodiments, the method is complete in less than 2 hours.

In one embodiment, in accordance with the principles of the present disclosure, a method is provided for preparing diphenol compounds having the formula:

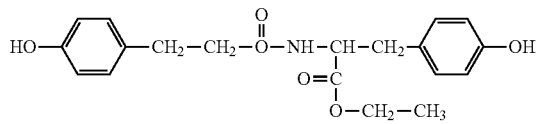

The method includes adding a hydroxyphenyl carboxylic acid having the formula:

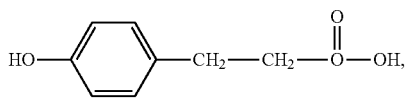

a tyrosine ethyl ester having the formula:

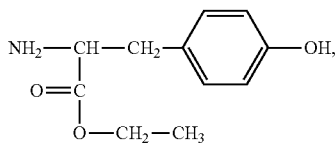

hydroxybenzotriazole hydrate and a solvent to a flask and stirring the contents of the flask to produce a first solution. EDCI HCl is added to the first solution to produce a first mixture. Ethyl acetate is added to the first mixture to produce a second mixture. The second mixture is added to sodium chloride to produce a third mixture having layer separation. An aqueous layer is removed from the third mixture. The third mixture is extracted with reagents after the aqueous layer has been removed from the third mixture to produce a fourth mixture. Magnesium sulfate is added to the fourth mixture to produce a fifth mixture. The fifth mixture is filtered to produce filtrate. The filtrate is concentrated. Crystallization of the concentrated filtrate is induced. Methylene chloride is added to the concentrated filtrate to produce a solid product. In some embodiments, the concentrated filtrate is not crystallized.

In one embodiment, in accordance with the principles of the present disclosure, a method is provided for preparing diphenol compounds having the formula:

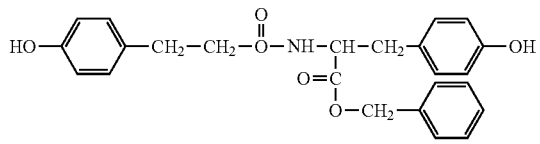

The method includes adding a hydroxyphenyl carboxylic acid having the formula:

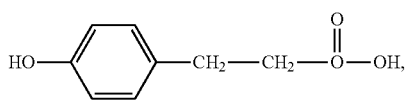

a paratoluene sulfonate salt of tyrosine benzyl ester having the formula:

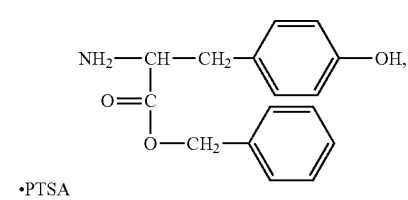 [SMILES: NC(Cc1ccc(O)cc1)C(=O)OCc1ccccc1]

hydroxybenzotriazole hydrate and a solvent to a flask and stirring the contents of the flask to produce a first mixture. Triethylamine is added to the first mixture to produce a second mixture. EDCI HCl is added to the second mixture to produce a third mixture. Ethyl acetate is added to the third mixture to produce a fourth mixture. The fourth mixture is added to distilled water to produce a fifth mixture having layer separation. An aqueous layer is removed from the fifth mixture. The fifth mixture is extracted with reagents after the aqueous layer has been removed from the fifth mixture to produce a sixth mixture. Magnesium sulfate is added to the sixth mixture to produce a seventh mixture. The seventh mixture is filtered to produce filtrate. The filtrate is concentrated. Crystallization of the concentrated filtrate is induced. Hexane is added to the crystallized filtrate to produce a solid product.

In some embodiments, the solvent is THF. In some embodiments, the solvent is a chlorinated solvent. In some embodiments, the solvent is removed by vacuum distillation. In some embodiments, the slurry, the mixtures, the filtrate and the solid product are maintained at about 5° C. to about 10° C. at all times during the method. In some embodiments, the method further comprises stirring the first mixture for about 15 minutes to about 30 minutes. In some embodiments, the slurry, the mixtures, the filtrate and the solid product are maintained at about 5° C. to about 10° C. It has been found that maintaining these components at about 5° C. to about 10° C. allows the amidation reaction to take place more rapidly and limit the amount of trimer formation than when the components are maintained at a higher temperature, such as, for example room temperature.

In some embodiments, the method is complete after about 1 hour to about 2 hours. In some embodiments, the method is complete in less than 2 hours.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

DETAILED DESCRIPTION

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention. While the invention will be described in conjunction with the embodiments discussed herein, it will be understood that the embodiments discussed herein are not intended to limit the invention to those embodiments. On the contrary, the invention is intended to cover all alternatives, modifications, and equivalents that may be included within the invention as defined by the appended claims.

In one embodiment, in accordance with the principles of the present disclosure, a method is provided for preparing a tyrosine ethyl ester having the formula:

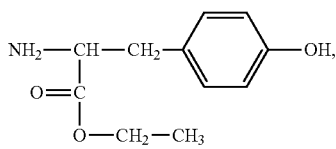

The method includes dissolving a tyrosine ethyl ester hydrochloride having the formula:

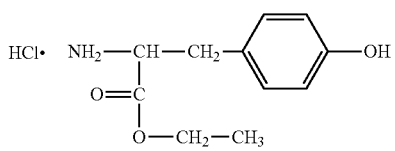

in distilled water to form a solution. The solution is mixed with methylene chloride to form a first mixture. Potassium carbonate is added to the first mixture to form a second mixture comprising separated layers. One of the separated layers is drawn off from the second mixture. Magnesium sulfate is added to the separated layer that was drawn off to form a third mixture. The methylene chloride is removed from the third mixture to form a slurry. Hexane is added to the slurry to form a solid. The solid is washed and dried.

In some embodiments, dissolving the tyrosine ethyl ester hydrochloride in distilled water comprises dissolving about 700 g to about 800 g of the tyrosine ethyl ester hydrochloride in about 2500 ml to about 3500 ml of distilled water. In some embodiments, dissolving the tyrosine ethyl ester hydrochloride in distilled water comprises dissolving about 745 g of the tyrosine ethyl ester hydrochloride in about 3034 ml of distilled water. In some embodiments, dissolving the tyrosine ethyl ester hydrochloride in distilled water comprises dissolving about 2.5 moles to about 3.5 moles of the tyrosine ethyl ester hydrochloride in about 2500 ml to about 3500 ml of distilled water. In some embodiments, dissolving the tyrosine ethyl ester hydrochloride in distilled water comprises dissolving about 3.03 moles of the tyrosine ethyl ester hydrochloride in about 3034 ml of distilled water. In some embodiments, the distilled water is pre-chilled at about 2° C. to about 5° C. In some embodiments, mixing the solution with methylene chloride comprises mixing about 4800 ml to about 5800 ml of methylene chloride with the solution. In some embodiments, mixing the solution with methylene chloride comprises mixing about 5342 ml of methylene chloride with the solution. In some embodiments, mixing the solution with methylene chloride comprises adding the methylene chloride to a separatory funnel; and adding the solution to the separatory funnel. In some embodiments, the separatory funnel is equipped with an overhead mixer. In some embodiments, mixing the solution and the methylene chloride comprises mixing the solution and the methylene chloride at a rate so as to afford homogeneity. The reactions are scalable to allow batches of different sizes to be made. For example, batches with less than about 5 kg of tyrosine ethyl ester, batches with between about 5 kg of tyrosine ethyl ester and about 20 kg of tyrosine ethyl ester, and batches with more than 20 kg of tyrosine ethyl ester can be made.

In some embodiments, the potassium carbonate comprises a 5M solution. In some embodiments, adding potassium carbonate to the first mixture comprises adding about 1100 ml to about 1300 ml of a 5M solution of potassium carbonate to the first mixture. In some embodiments, adding potassium carbonate to the first mixture comprises adding about 1214 ml of a 5M solution of potassium carbonate to the first mixture. In some embodiments, adding potassium carbonate to the first mixture comprises adding about 5.5 moles to about 6.5 moles of potassium carbonate to the first mixture. In some embodiments, adding potassium carbonate to the first mixture comprises adding about 6.07 moles of potassium carbonate to the first mixture. In some embodiments, the potassium carbonate is added to the first mixture over a period of about 10 minutes. In some embodiments, drawing off one of the separated layers comprises drawing off a lower product layer of the separated layers.

In some embodiments, adding magnesium sulfate to the separated layer that was drawn off comprises adding about 25 grams to about 35 grams of anhydrous magnesium sulfate to the second mixture; mixing the magnesium sulfate and the second mixture for about 10 minutes; and adding about 25 grams to about 35 grams of additional anhydrous magnesium sulfate to the mixed magnesium sulfate and second mixture to form the third mixture. In some embodiments, adding magnesium sulfate to the separated layer that was drawn off comprises adding about 30 grams of anhydrous magnesium sulfate to the second mixture; mixing the magnesium sulfate and the second mixture for about 10 minutes; and adding about 30 grams of additional anhydrous magnesium sulfate to the mixed magnesium sulfate and second mixture to form the third mixture. In some embodiments, the method further comprises mixing the third mixture for about 1 hour; and allowing the mixed third mixture to stand for about 1 hour. In some embodiments, the method further comprises filtering the third mixture. In some embodiments, the methylene chloride is removed from the third mixture by vacuum distillation. In some embodiments, the methylene chloride is removed from the third mixture by vacuum distillation at a temperature that is less than or equal to about 40° C.

In some embodiments, the method further comprises cooling the slurry to room temperature prior to adding hexane to the slurry. In some embodiments, adding hexane to the slurry comprises adding about 4 liters to about 6 liters of hexane to the slurry and stirring for about 1 hour to about 3 hours. In some embodiments, adding hexane to the slurry comprises adding about 5 liters of hexane to the slurry and stirring for about 1 hour to about 3 hours. In some embodiments, the method further comprises isolating the solid by vacuum filtration. In some embodiments, the method further comprises washing the precipitate with hexane. In some embodiments, the precipitate is washed with 2× stationary overflow portions of hexane. In some embodiments, the method further comprises drying the solid. In some embodiments, the method further comprises drying the solid at less than about 1 mm Hg and room temperature.

In one embodiment, in accordance with the principles of the present disclosure, a method is provided for preparing diphenol compounds having the formula:

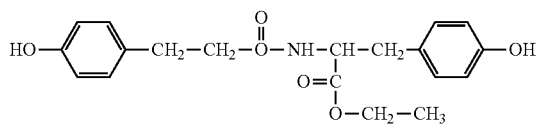

The method includes adding a hydroxyphenyl carboxylic acid having the formula:

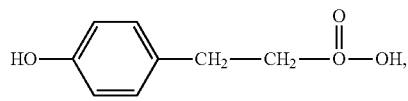

a tyrosine ethyl ester having the formula:

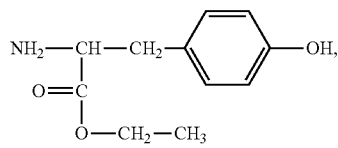

hydroxybenzotriazole hydrate and a solvent to a flask and stirring the contents of the flask to produce a first solution. EDCI HCl is added to the first solution to produce a first mixture. Ethyl acetate is added to the first mixture to produce a second mixture. The second mixture is added to sodium chloride to produce a third mixture having layer separation. An aqueous layer is removed from the third mixture. The third mixture is extracted with reagents after the aqueous layer has been removed from the third mixture to produce a fourth mixture. Magnesium sulfate is added to the fourth mixture to produce a fifth mixture. The fifth mixture is filtered to produce filtrate. The filtrate is concentrated. Crystallization of the concentrated filtrate is induced. Methylene chloride is added to the crystallized filtrate to produce a solid product. In some embodiments, the diphenol compound has the chemical formula $C_{20}H_{23}NO_5$ and has a molecular weight of 357.4.

In some embodiments, the solvent is N-methylpyrrolidinone. In some embodiments, the solvent is a polar solvent. In some embodiments, the solvent is THF. In some embodiments, the solvent is a chlorinated solvent. In some embodiments, the first solution is a clear solution. In some embodiments, the contents of the flask are stirred for about 15 minutes to about 30 minutes. In some embodiments, the flask is a 5 liter 3-necked flask.

In some embodiments, the first solution comprises at least about 2% excess of the tyrosine ethyl ester relative to the hydroxyphenyl carboxylic acid. In some embodiments, the first solution comprises an increased molar amount of the tyrosine ethyl ester relative to the hydroxyphenyl carboxylic acid. In some embodiments, the first solution comprises equal molar amounts of the tyrosine ethyl ester and the hydroxyphenyl carboxylic acid. It has been found that increasing the molar amount of the tyrosine ethyl ester allows the reaction to be preferentially driven towards amidation rather than esterification. As little as about 2% excess of the tyrosine ethyl ester has been found to be sufficient to reduce the side product to less than about 0.5% compared to about 3% to about 5% if an equimolar amount is used. Indeed, when the tyrosine ethyl ester and the hydroxyphenyl carboxylic acid have a molar ratio of 1:0.9 the trimer ratio is 2.4%; when the tyrosine ethyl ester and the hydroxyphenyl carboxylic acid have a molar ratio of 1:1.03 the trimer ratio is 0.32%; and when the tyrosine ethyl ester and the hydroxyphenyl carboxylic acid have a molar ratio of 1.2:1 the trimer ratio is 15.07. If excess of the hydroxyphenyl carboxylic acid is used, higher amounts of the esterified product will be formed and should hence be avoided.

In some embodiments, about 380 g to about 480 g of the tyrosine ethyl ester, about 300 g to about 400 g of the hydroxyphenyl carboxylic acid, about 20 g to about 40 g of the hydroxybenzotriazole hydrate and about 1200 ml to about 1300 ml of the solvent are added to the flask to form the first solution. In some embodiments, about 431 g of the tyrosine ethyl ester, about 339 g of the hydroxyphenyl carboxylic acid, about 28.8 g of the hydroxybenzotriazole hydrate and about 1200 ml to about 1300 ml of the solvent are added to the flask to form the first solution. In some embodiments, about 1.5 moles to about 2.5 moles of the tyrosine ethyl ester, about 1.5 moles to about 2.5 moles of the hydroxyphenyl carboxylic acid, about 0.15 moles to about 2.5 moles of the hydroxybenzotriazole hydrate and about 1200 ml to about 1300 ml of the solvent are added to the flask to form the first solution. In some embodiments, about 2.06 moles of the tyrosine ethyl ester, about 2.04 moles of the hydroxyphenyl carboxylic acid, about 0.19 moles of the hydroxybenzotriazole hydrate and about 1200 ml to about 1300 ml of the solvent are added to the flask to form the first solution. In some embodiments, the tyrosine ethyl ester is added to the flask and the hydroxyphenyl carboxylic acid is metered into the flask after the tyrosine ethyl ester is added to the flask. Indeed, for the esterification to take place there must always be free carboxylic acids present so that more can react with the amine group. In some embodiments, esterification is limited by changing the sequence of addition. In particular, rather than adding the hydroxyphenyl carboxylic acid and the tyrosine ester before the coupling agent (e.g., EDCI HCl) is added, the method may be modified so that only the tyrosine ethyl ester is present at the start and the hydroxyphenyl carboxylic acid is metered in during the course of the reaction. This ensures that there are always excess amine groups present, which will favor amidation. In some embodiments, the reaction time for the metering is about 2 hours.

In some embodiments, an excess, such as, for example, a slight excess of the EDCI HCl is used. In some embodiments, the amount of the EDCI HCl used is reduced to a molar equivalent or about 10% less. It has been found that reducing the amount of the EDCI HCl used will ensure a cleaner reaction since the amine will consume all of the EDCI HCl and limit esterification. In some embodiments, an equimolar amount of the EDCI HCl and the hydroxyphenyl carboxylic acid is prepared in the reaction medium. The EDCI HCl and the hydroxyphenyl carboxylic acid are added drop wise into the flask, wherein the flask includes the tyrosine ethyl ester, the hydroxybenzotriazole hydrate and/or the solvent. It has been found that this allows the hydroxyphenyl carboxylic acid to be immediately consumed by the tyrosine ethyl ester. As such, even if there was any excess of the hydroxyphenyl carboxylic acid, there will be no coupling agent available to cause the esterification reaction.

In some embodiments, the method further comprises cooling the flask using an ice water bath and stirring the first solution in the cooled flask for about 20 minutes prior to adding EDCI to the first solution. In some embodiments, the EDCI is added to one portion of the stirred first solution.

In some embodiments, the method further comprises washing the first solution with about 100 ml to about 200 ml of N-methylpyrrolidinone after the EDCI is added to one portion of the stirred first solution. In some embodiments, the method further comprises capping the flask and stirring the first mixture for about 4 hours; and allowing the temperature of the first mixture to reach room temperature. In some embodiments, the first mixture is allowed to reach room temperature without replenishing ice to the ice bath. In some embodiments, the method further comprises stirring the first mixture overnight after the first mixture reaches room temperature. In some embodiments, the first solution, the mixtures, the filtrate and the solid product are maintained at about 5° C. to about 10° C. It has been found that higher temperature leads to higher trimer content. For example, when the reaction temperature is about 30° C., the trimer ratio is 0.48%. However, when the reaction temperature is about 5° C., the trimer ratio is 0.16%. As such, maintaining these components at about 5° C. to about 10° C. allows the amidation reaction to take place more rapidly and limit the amount of trimer formation than when the components are maintained at a higher temperature, such as, for example room temperature.

In some embodiments, adding ethyl acetate to the first mixture comprises adding about 2000 ml to about 3000 ml of ethyl acetate to the first mixture. In some embodiments, adding ethyl acetate to the first mixture comprises adding about 2600 ml of ethyl acetate to the first mixture. In some embodiments, adding ethyl acetate to the first mixture comprises adding about 2000 ml to about 3000 ml of ethyl acetate to the first mixture and stirring the second mixture for about 15 minutes. In some embodiments, adding ethyl acetate to the first mixture comprises adding about 2600 ml of ethyl acetate to the first mixture and stirring the second mixture for about 15 minutes. In some embodiments, adding sodium chloride to the second mixture comprises transferring the second mixture to a separatory funnel including sodium chloride. In some embodiments, the separatory funnel is a 12 liter separatory funnel already containing about 2000 ml to about 3000 ml of 20% sodium chloride. In some embodiments, the method further comprises stirring the third mixture with an overhead mixer to afford homogeneity. In some embodiments, the separatory funnel is a 12 liter separatory funnel already containing about 2600 ml of 20% sodium chloride. In some embodiments, the method further comprises stirring the third mixture with an overhead mixer to afford homogeneity.

In some embodiments, the reagents used to extract the third mixture comprise: a first reagent comprising sodium bicarbonate and sodium chloride; a second reagent comprising sodium bicarbonate and sodium chloride; a third reagent comprising HCl and sodium chloride; a fourth reagent comprising sodium chloride; a fifth reagent comprising sodium bicarbonate and sodium chloride; and a sixth reagent comprising sodium chloride. In some embodiments, the first reagent comprises 1× about 2000 ml to about 3000 ml of 3% sodium bicarbonate and about 14% sodium chloride; the second reagent comprises 1× about 800 ml to about 1500 ml of 3% sodium bicarbonate and about 14% sodium chloride; the third reagent comprises 3× about 800 ml to about 1600 ml of 0.4 M HCl and about 20% sodium chloride; the fourth reagent comprises 1×1200 ml of about 20% sodium chloride; the fifth reagent comprises 1× about 800 ml to about 1600 ml of about 3% sodium bicarbonate and about 14% sodium chloride; and the sixth reagent comprises 1× about 800 ml to about 1600 ml of about 20% sodium chloride.

In some embodiments, the reagents used to extract the third mixture comprise: a first reagent comprising sodium bicarbonate and sodium chloride; a second reagent comprising sodium bicarbonate and sodium chloride; a third reagent comprising HCl and sodium chloride; a fourth reagent comprising sodium chloride; a fifth reagent comprising sodium bicarbonate and sodium chloride; and a sixth reagent comprising sodium chloride. In some embodiments, the first reagent comprises 1×2600 ml of 3% sodium bicarbonate and about 14% sodium chloride; the second reagent comprises 1×1200 ml of 3% sodium bicarbonate and about 14% sodium chloride; the third reagent comprises 3×1200 ml of 0.4 M HCl and about 20% sodium chloride; the fourth reagent comprises 1×1200 ml of about 20% sodium chloride; the fifth reagent comprises 1×1200 ml of about 3% sodium bicarbonate and about 14% sodium chloride; and the sixth reagent comprises 1×1200 ml of about 20% sodium chloride. In some embodiments, the method further comprises drawing off an upper ethyl acetate layer of the fourth mixture prior to adding magnesium sulfate to the fourth mixture. In some embodiments, the method further comprises stirring the fifth mixture for about 5 minutes; allowing the fifth mixture to stand in a covered flask for at least one hour; and filtering the fifth mixture. In some embodiments, the method further comprises concentrating the filtrate prior to inducing crystallization of the filtrate. In some embodiments, the filtrate is concentrated by rotary evaporation. In some embodiments, the filtrate is maintained at a temperature that is less than about 45° while the filtrate is concentrated.

In some embodiments, inducing crystallization of the filtrate comprises pouring the concentrated filtrate into a kettle and seeding the concentrated filtrate with the diphenol compound. In some embodiments, adding methylene chloride to the crystallized filtrate comprises adding about 3 liters to about 4 liters of methylene chloride to the crystallized filtrate and stirring in an enclosed kettle until a smooth fine suspension results. In some embodiments, adding methylene chloride to the crystallized filtrate comprises adding about 3.5 liters of methylene chloride to the crystallized filtrate and stirring in an enclosed kettle until a smooth fine suspension results. In some embodiments, the crystallized filtrate and methylene chloride is stirred for about 6 hours to about 24 hours. In some embodiments, the method further comprises: filtering the solid product; washing the filtered solid product with 2× stationary overflow portions of methylene chloride; and drying the washed solid product. In some embodiments, the solid product is dried at about 50° C. and less than 1 mm Hg.

It has been found that higher reaction times lead to higher trimer content. For example, a reaction time of about 20 hours produces 0.71% of the timer, while a reaction time of about 2 hours produces 0.37% of the trimer. As such, in some embodiments, the method is complete after about 1 hour to about 2 hours. In some embodiments, the method is complete in less than 2 hours. It has been found that shortening the reaction times from 24 hours to about 1 hour to about 2 hours will lower trimer content in the monomer since amidation is thermodynamically favored over esterification.

In some embodiments, the tyrosine ethyl ester is liberated and is used without isolation. For this, a tyrosine ethyl ester hydrochloride having the formula:

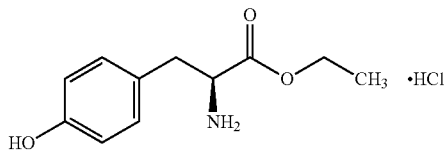

is suspended or dissolved in a reaction medium. An equimolar amount of an organic base, such as, for example, N-ethyl morpholine or triethyl amine is added and the reaction mixture is stirred for about 1 hour. The free base is liberated and dissolves in the reaction medium. The hydroxylphenyl carboxylic acid, hydroxybenzotriazole hydrate and a solvent are added to the reaction medium and are stirred to produce a first solution. EDCI HCl is added to the first solution to produce a first mixture. Ethyl acetate is added to the first mixture to produce a second mixture. The second mixture is added to sodium chloride to produce a third mixture having layer separation. An aqueous layer is removed from the third mixture. The third mixture is extracted with reagents after the aqueous layer has been removed from the third mixture to produce a fourth mixture. Magnesium sulfate is added to the fourth mixture to produce a fifth mixture. The fifth mixture is filtered to produce filtrate. The filtrate is concentrated. Crystallization of the concentrated filtrate is induced. Methylene chloride is added to the crystallized filtrate to produce a solid product. This allows the diphenol compound to be directly synthesized.

In some embodiments, a side product of the reaction, such as, for example, the triethylamine HCl having the formula:

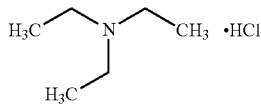

is insoluble in the reaction medium if a solvent such as THF is used. In such embodiments, the salt may be filtered off prior to adding the other reagents. In some embodiments, the tyrosine ethyl ester hydrochloride is in slight excess of the organic amine, such as, for example, between about 0.5% to about 2% in excess to ensure that all of the organic base has been used up since these bases can catalyze side reactions and generate impurities. In some embodiments, the reaction medium is analyzed using a suitable analytical method, such as, for example, High Performance Liquid Chromatography or Gas Chromatography to accurately determine the concentration of the tyrosine ethyl ester.

In one embodiment, in accordance with the principles of the present disclosure, a method is provided for preparing diphenol compounds having the formula:

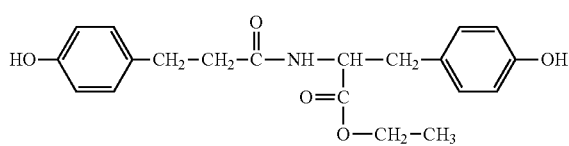

The method includes adding a hydroxyphenyl carboxylic acid having the formula:

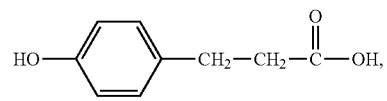 [SMILES: O=C(O)CCc1ccc(O)cc1]

a paratoluene sulfonate salt of tyrosine ethyl ester having the formula:

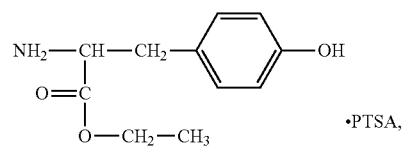

hydroxybenzotriazole hydrate and a solvent to a flask and stirring the contents of the flask to produce a first solution. EDCI HCl is added to the first solution to produce a first mixture. Ethyl acetate is added to the first mixture to produce a second mixture. The second mixture is added to sodium chloride to produce a third mixture having layer separation. An aqueous layer is removed from the third mixture. The third mixture is extracted with reagents after the aqueous layer has been removed from the third mixture to produce a fourth mixture. Magnesium sulfate is added to the fourth mixture to produce a fifth mixture. The fifth mixture is filtered to produce filtrate. The filtrate is concentrated. Crystallization of the concentrated filtrate is induced. Methylene chloride is added to the concentrated filtrate to produce a solid product. In some embodiments, the solid is slurried repeatedly with methylene chloride and filtered to reduce the amount of side products that may be formed. In some embodiments, the concentrated filtrate is not crystallized. In some embodiments, the solid is slurried repeatedly with methylene chloride and filtered. This reduces the amount of side products that may have been formed.

In some embodiments, the concentrated filtrate is crystallized by adding a mixture of methylene chloride and Toluene 10:3. In these embodiments, the ethyl acetate is evaporated until the concentration of DTE is about 15%. 100 ml of methyl chloride and 30 ml of toluene is added for every 10 g of the DTE at a concentration of 15%. The mixture of DTE, methyl chloride and toluene is stirred for up to 48 hours until all of the material has crystallized. The solid is isolated. The same technique can be employed for the isolated DTE, which has a high trimer content.

In one embodiment, in accordance with the principles of the present disclosure, a method is provided for preparing diphenol compounds having the formula:

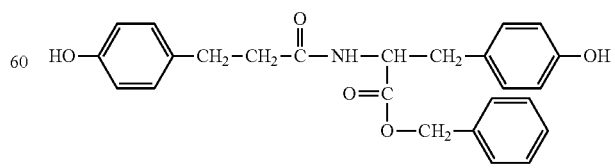

The method includes adding a hydroxyphenyl carboxylic acid having the formula:

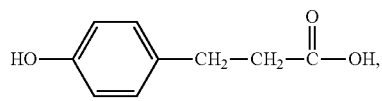

a paratoluene sulfonate salt of tyrosine benzyl ester having the formula:

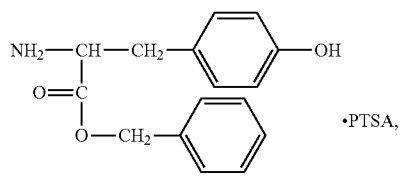

·PTSA, hydroxybenzotriazole hydrate and a solvent to a flask and stirring the contents of the flask to produce a first mixture. Triethylamine is added to the first mixture to produce a second mixture. EDCI HCl is added to the second mixture to produce a third mixture. Ethyl acetate is added to the third mixture to produce a fourth mixture. The fourth mixture is added to distilled water to produce a fifth mixture having layer separation. An aqueous layer is removed from the fifth mixture. The fifth mixture is extracted with reagents after the aqueous layer has been removed from the fifth mixture to produce a sixth mixture. Magnesium sulfate is added to the sixth mixture to produce a seventh mixture. The seventh mixture is filtered to produce filtrate. The filtrate is concentrated. Crystallization of the concentrated filtrate is induced. Hexane is added to the crystallized filtrate to produce a solid product. In some embodiments, the diphenol compound has the chemical formula $C_{25}H_{25}NO_5$ and has a molecular weight of 419.47.

In some embodiments, the first mixture is a smooth slurry. In some embodiments, the contents of the flask are stirred for about 15 minutes to about 30 minutes. In some embodiments, the solvent is N-methylpyrrolidinone. In some embodiments, the solvent is a polar solvent. In some embodiments, the solvent is THF. In some embodiments, the solvent is a chlorinated solvent. In some embodiments, about 350 g to about 450 g of the tyrosine benzyl ester, about 35 g to about 50 g of the hydroxyphenyl carboxylic acid, about 5 g to about 15 g of the hydroxybenzotriazole hydrate and about 150 ml to about 350 ml of the solvent are added to the flask to form the slurry. In some embodiments, about 391.3 g of the tyrosine benzyl ester, about 43.4 g of the hydroxyphenyl carboxylic acid, about 10.96 g of the hydroxybenzotriazole hydrate and about 250 ml of the solvent are added to the flask to form the slurry. In some embodiments, about 0.75 moles to about 0.95 moles of the tyrosine benzyl ester, about 0.75 moles to about 0.95 moles of the hydroxyphenyl carboxylic acid, about 0.075 moles to about 0.095 moles of the hydroxybenzotriazole hydrate and about 250 ml of the solvent are added to the flask to form the slurry. In some embodiments, about 0.8823 moles of the tyrosine benzyl ester, about 0.8632 moles of the hydroxyphenyl carboxylic acid, about 0.088 moles of the hydroxybenzotriazole hydrate and about 150 ml to about 350 ml of the solvent are added to the flask to form the slurry. In some embodiments, the method further comprises stirring the first mixture for about 15 minutes to about 30 minutes.

In some embodiments, the method further comprises: cooling flask using an ice water bath after stirring the first mixture; and stirring the first mixture in the cooled flask for about 20 minutes. In some embodiments, adding triethylamine to the first mixture comprises adding about 100 ml to about 130 ml of triethylamine to the first mixture. In some embodiments, adding triethylamine to the first mixture comprises adding about 123.3 ml of triethylamine to the first mixture. In some embodiments, adding triethylamine to the first mixture comprises adding about 0.75 moles to about 0.95 moles of triethylamine to the first mixture. In some embodiments, adding triethylamine to the first mixture comprises adding about 0.884 moles of triethylamine to the first mixture. In some embodiments, adding EDCI HCl to the second mixture comprises adding EDCI HCl to one portion of the stirred first mixture in the cooled flask. In some embodiments, an excess, such as, for example, a slight excess of the EDCI HCl is used. In some embodiments, the amount of the EDCI HCl used is reduced to a molar equivalent or about 10% less. It has been found that reducing the amount of the EDCI HCl used will ensure a kinetically faster reaction since the amine will consume all of the EDCI HCl and limit esterification. In some embodiments, an equimolar amount of the EDCI HCl and the hydroxyphenyl carboxylic acid is prepared in the reaction medium (e.g., the flask). The EDCI HCl and the hydroxyphenyl carboxylic acid are added drop wise into the flask, wherein the flask includes the tyrosine benzyl ester, the hydroxybenzotriazole hydrate and/or the solvent. It has been found that this allows the hydroxyphenyl carboxylic acid to be immediately consumed by the tyrosine benzyl ester. As such, even if there was any excess of the hydroxyphenyl carboxylic acid, there will be no coupling agent available to cause the esterification reaction. In some embodiments, the slurry comprises an increased molar amount of the tyrosine benzyl ester relative to the hydroxyphenyl carboxylic acid. In some embodiments, the slurry comprises equal molar amounts of the tyrosine benzyl ester and the hydroxyphenyl carboxylic acid. It has been found that increasing the molar amount of the tyrosine benzyl ester allows the reaction to be preferentially driven towards amidation rather than esterification. As little as about 2% excess of the tyrosine benzyl ester has been found to be sufficient to reduce the side product to less than about 0.5% compared to about 3% to about 5% if an equimolar amount is used. If excess of the hydroxyphenyl carboxylic acid is used, higher amounts of the esterified product will be formed and should hence be avoided.

In some embodiments, the method further comprises washing the third mixture with about 200 ml to about 300 ml of ethyl acetate after adding EDCI HCl to one portion of the stirred first mixture in the cooled flask. In some embodiments, the method further comprises washing the third mixture with about 100 ml of ethyl acetate after adding EDCI HCl to one portion of the stirred first mixture in the cooled flask. In some embodiments, the method further comprises: capping the flask and stirring the third mixture for about 4 hours; and allowing the temperature of the third mixture to reach room temperature. In some embodiments, the third mixture is allowed to reach room temperature without replenishing ice to the ice bath. In some embodiments, the method further comprises stirring the third mixture overnight after the first mixture reaches room temperature.

In some embodiments, the slurry, the mixtures, the filtrate and the solid product are maintained at about 5° C. to about 10° C. It has been found that higher temperatures lead to higher trimer content. For example, when the reaction temperature is about 30° C., the trimer ratio is 0.48%. However, when the reaction temperature is about 5° C., the trimer ratio is 0.16%. As such, maintaining these components at about 5° C. to about 10° C. allows the amidation reaction to take place more rapidly and limit the amount of trimer formation than when the components are maintained at a higher temperature, such as, for example room temperature.

In some embodiments, adding ethyl acetate to the third mixture comprises adding about 1500 ml to about 2500 ml of ethyl acetate to the third mixture and stirring the fourth mixture for about 1 hour. In some embodiments, adding ethyl acetate to the third mixture comprises adding about 1956 ml of ethyl acetate to the third mixture and stirring the fourth mixture for about 1 hour. In some embodiments, adding the fourth mixture to distilled water comprises adding the fourth mixture to a separatory funnel including distilled water. In some embodiments, the separatory funnel is a 22 liter separatory funnel already containing about 2000 ml of distilled water. In some embodiments, the method further comprises stirring the fourth mixture with an overhead mixer to afford homogeneity.

In some embodiments, the reagents used to extract the fifth mixture comprise: a first reagent comprising sodium bicarbonate; a second reagent comprising sodium chloride; a third reagent comprising HCl; and a fourth reagent comprising sodium chloride. In some embodiments, the first reagent comprises 3× about 400 ml to about 600 ml of 0.5 M sodium chloride; the second reagent comprises 1× about 400 ml to about 600 ml of 20% sodium chloride; the third reagent comprises 3× about 400 ml to about 600 ml of 0.2 M HCl; and the fourth reagent comprises 1× about 400 ml to about 600 ml of 20% sodium chloride. In some embodiments, the reagents used to extract the fifth mixture comprise: a first reagent comprising sodium bicarbonate; a second reagent comprising sodium chloride; a third reagent comprising HCl; and a fourth reagent comprising sodium chloride. In some embodiments, the first reagent comprises 3×500 ml of 0.5 M sodium chloride; the second reagent comprises 1×500 ml of 20% sodium chloride; the third reagent comprises 3×500 ml of 0.2 M HCl; and the fourth reagent comprises 1×500 ml of 20% sodium chloride.

In some embodiments, the method further comprises drawing off an upper ethyl acetate layer of the sixth mixture prior to adding magnesium sulfate to the sixth mixture. In some embodiments, the method further comprises: stirring the seventh mixture for about 30 minutes; allowing the seventh mixture to stand in a covered flask for at least one hour; and filtering the seventh mixture. In some embodiments, the method further comprises concentrating the filtrate prior to inducing crystallization of the filtrate. In some embodiments, the filtrate is concentrated by vacuum distillation. In some embodiments, the filtrate is maintained at a temperature that is less than about 45° C. while the filtrate is concentrated. In some embodiments, inducing crystallization of the filtrate comprises pouring the concentrated filtrate into a kettle and seeding the concentrated filtrate with about 50 mg to about 100 mg of the diphenol compound. In some embodiments, adding hexane to the crystallized filtrate comprises adding about 0.8 liters to about 1.2 liters of hexane to the crystallized filtrate and stirring. In some embodiments, adding hexane to the crystallized filtrate comprises adding about 1 liter of hexane to the crystallized filtrate and stirring. In some embodiments, the crystallized filtrate and hexane is stirred for about 4 hours. In some embodiments, the method further comprises: filtering the solid product; washing the filtered solid product with 2× stationary overflow portions of hexane; and drying the washed solid product. In some embodiments, the solid product is dried at about 50° C. and less than 1 mm Hg.

It has been found that higher reaction times lead to higher trimer content. For example, a reaction time of about 20 hours produces 0.71% of the timer, while a reaction time of about 2 hours produces 0.37% of the trimer. As such, in some embodiments, the method is complete after about 1 hour to about 2 hours. In some embodiments, the method is complete in less than 2 hours. It has been found that shortening the reaction times from 24 hours to about 1 hour to about 2 hours will lower trimer content in the monomer since amidation is thermodynamically favored over esterification.

It has been found that the difunctionality of the diphenol having the formula:

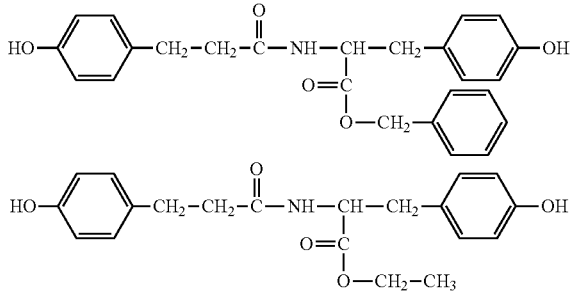

may help to achieve high molecular weight. Indeed, if the phenolic group is absent or protected, it will not be reactive in the next step, thus resulting in lower yield. If this unreacted compound is not removed in the purification step, it will get carried over to a polymerization step wherein the monomers discussed herein are used to form a polymer. The unreacted compound will function as a chain terminator in the polymerization step since it has only one reactive phenolic group. If the phenolic group is absent or protected, it will couple with the amine during synthesis of the monomers discussed herein. However, the resulting compound will behave as a monofunctional phenol in the synthesis step, thus limiting polymerization. As such, in some embodiments, one or more of the methods discussed herein include purifying a hydroxyphenyl carboxylic acid having the formula:

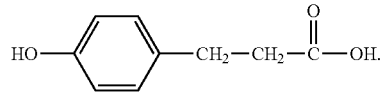

In some embodiments, to purify the hydroxyphenyl carboxylic acid, it is recrystallized from a mixture of toluene and ethyl acetate. In some embodiments, the mixture is heated and then filtered without immediate recrystallization.

In some embodiments, wherein the reaction takes place in THF, NMP and/or another water soluble solvent, the hydroxyphenyl carboxylic acid is purified by adding the reaction mixture into water and stirring to get a solid. The solid is then reslurried in dilute HCl until acidic. The reslurried solid is diluted in water and NaHCO$_3$ until it is basic. Water is added until it is neutral and the solid is dried.

In one embodiment, in accordance with the principles of the present disclosure, a method is for preparing diphenol compounds having the formulas:

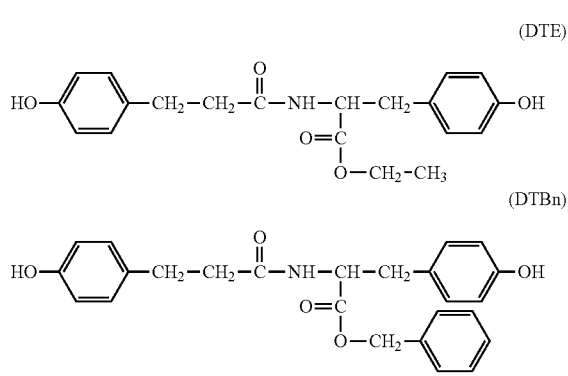

(DTE)

(DTBn)

is provided. In this embodiment, both of the diphenol compounds are prepared in the same pot.

The method includes combining a tyrosine ethyl ester hydrochloride having the formula:

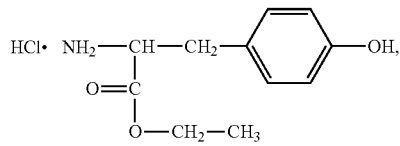

with a tyrosine benzyl ester having the formula:

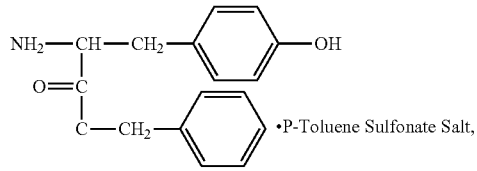 [SMILES: NC(Cc1ccc(O)cc1)C(=O)CCc1ccccc1]
·P-Toluene Sulfonate Salt, with a hydroxy phenyl carboxylic acid having the formula

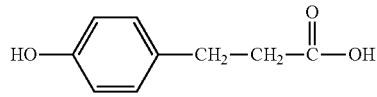 [SMILES: O=C(O)CCc1ccc(O)cc1]

to obtain a mixture of the two diphenols DTE and DTBn.

In some embodiments, the ratio of the tyrosine ethyl ester hydrochloride and the tyrosine benzyl ester are directly proportional to the ratio of DTE and DTBn in the final product. For example, to make 75% DTE and 25% DTBn, the copolymer comprises 75% of the tyrosine ethyl ester hydrochloride and 25% of the tyrosine benzyl ester. Conversely, to make 25% DTE and 75% DTBn, the copolymer comprises 25% of the tyrosine ethyl ester hydrochloride and 75% of the tyrosine benzyl ester.

One mole of trimethylamine is added to the mixture of diphenols to produce a mixture. One mole each of:

(a) a hydroxyphenyl carboxylic acid having the formula:

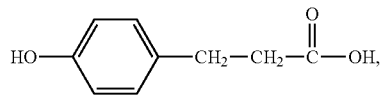

(b) EDCI, and
(c) Hydroxybenzotriazole is added to the mixture to produce a first solution.

EDCI HCl is added to the first solution to produce a first mixture. Ethyl acetate is added to the first mixture to produce a second mixture. The second mixture is added to sodium chloride to produce a third mixture having layer separation. An aqueous layer is removed from the third mixture. The third mixture is extracted with reagents after the aqueous layer has been removed from the third mixture to produce a fourth mixture. Magnesium sulfate is added to the fourth mixture to produce a fifth mixture. The fifth mixture is filtered to produce filtrate. The filtrate is concentrated. Crystallization of the concentrated filtrate is induced. Methylene chloride is added to the concentrated filtrate to produce a solid product.

It is envisioned that the reactions discussed herein may be run in a small scale or a large scale, without changing the method. In some embodiments, the reactions are run in a multi-kilogram scale with reactors, such as, for example 50 gallon reactors.

Example 1

A tyrosine ethyl ester having the formula:

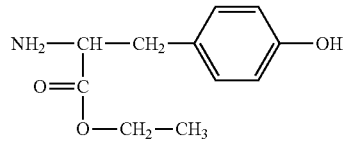

was synthesized using the materials in Table 1.

TABLE 1

| Reagent | Amount (moles) |
| --- | --- |
| TE·HCl | 745 g (3.03) |
| K2CO3 (5M solution) | 1214 ml (6.07) |
| Water | 3034 ml |
| Methylene chloride | 5342 ml |
| Hexane | 5 liters |
| Anhydrous MgSO4 | 30 g |

The TE.HCl has the formula:

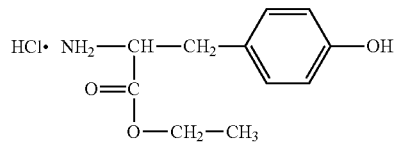

To synthesize the tyrosine ethyl ester, the TE.HCl was dissolved in distilled water that was pre-chilled at 2-5° C. While the solid (TE.HCl) was dissolving, the methylene chloride was added to a separatory equipped with an overhead mixer. As soon as the solid has dissolved, the solution was added to the separatory funnel and was mixed at such a rate so as to afford homogeneity. The potassium carbonate solution was added to the well stirred mixture over a period of 10 min. After the layers have separated, the lower product layer was drawn off. 30 g of anhydrous magnesium sulfate was added to the methylene chloride solution and mixed for 10 minutes. Another 30 g of MgSO4 was added, mixed slowly for 1 h and allowed to stand for 1 h. The mixture was then filtered. The methylene chloride was removed by vacuum distillation at a temp not to exceed 40° C. After cooling to room temperature, 5 L of hexane was added and stirred for 1-3 h. The solid (tyrosine ethyl ester) was isolated by vacuum filtration. The precipitate (solid tyrosine ethyl ester) was washed with 2× stationary overflow portions of hexane. The solid was dried at <1 mmHg and at room temperature. The yield of the solid was 480-500 g.

Example 2

A desamino tyrosyl tyrosine ethyl ester having the formula:

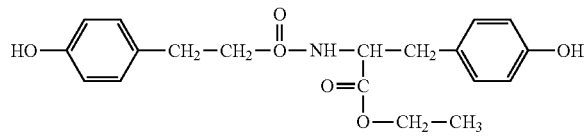

was synthesized using the materials in Table 2.

TABLE 2

| Reagents | Amount (moles) |
| --- | --- |
| Tyrosine ethyl ester (TE) | 431 g (2.06) |
| DAT | 339 g (2.04) |
| Hydroxybenzotriazole hydrate (HOBT•H$_2$O) | 28.8 g (0.19) Hydrate |
| N-methylpyrrolidinone (NMP) | 1409 ml |
| EDCl•HCl | 417 g (2.18) |
| Ethyl acetate | 2.5 liters |
| Methylene chloride | 4 liters |
| Sodium chloride | 20% and 14% |
| Sodium bicarbonate | 3% |
| HCl | 0.4M |
| Anhydrous magnesium sulfate | 50 g |

TE has the formula:

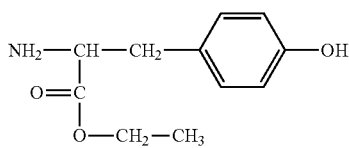

DAT has the formula:

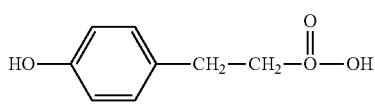

To synthesize the desamino tyrosyl tyrosine ethyl ester, DAT, TE, HOBT and about 1200-1300 ml of the NMP were added to a 5 liter 3-necked flask and were stirred with a mechanical stirrer until a clear solution was obtained (about 15-30 minutes). The flask was cooled using an ice water bath and was stirred for about 20 minutes in the cold. EDCI was added in one portion to the stirred reaction mixture. The reaction mixture was washed down with the remaining NMP. The flask was capped and stirred for 4 h, allowing the temperature to reach room temperature (25° C.) in the ice-bath without replenishing the melting ice. The reactor was stirred overnight at room temperature. Ethyl acetate (2600 ml) was added to the reactor and stirred for about 15 minutes. The entire reaction mixture was transferred to a 12 L separatory funnel already containing 2600 ml of 20% sodium chloride (200 g diluted to 1 L). The funnel contents were stirred with an overhead mixer to afford homogeneity. After layer separation was been achieved, the lower aqueous layer was drawn off and discarded. The ethyl acetate solution was extracted with the following reagents in the order indicated:

a. 1×2600 ml of 3% sodium bicarbonate/14% sodium chloride (30 g sodium bicarbonate/140 g sodium chloride diluted to 1 L);

b. 1×1200 ml of 3% sodium bicarbonate/14% sodium chloride;

c. 3×1200 ml of 0.4 M HCl/20% sodium chloride (33.3 ml concentrated HCl/200 g sodium chloride diluted to 1 L);

d. 1×1200 ml of 20% sodium chloride;

e. 1×1200 ml of 3% sodium bicarbonate/14% sodium chloride; and f. 1×1200 ml of 20% sodium chloride.

The upper ethyl acetate layer was drawn off and 50 g of anhydrous magnesium sulfate was added and stirred for 5 minutes. The mixture was allowed to stand in the covered flask for at least 1-2 h. The mixture was then filtered. The filtrate was concentrated by rotary evaporation to a thick but mobile liquid. Temperature of the solution during concentration did not exceed 45° C. The thick liquid was poured into a 5 L resin kettle and was seeded with <50 mg of DTE to induce crystallization. After the solid crystallized, 3.5 L of methylene chloride was added to the solid and was stirred in the enclosed kettle until a smooth fine suspension results (6-24 h). The solid product was filtered and washed with 2× stationary overflow portions of methylene chloride. The solid product was dried at 50° C. and <1 mmHg. The yield of the solid was 600 g (82%).

Example 3

Desamino tyrosyl tyrosine benzyl esters having the formula:

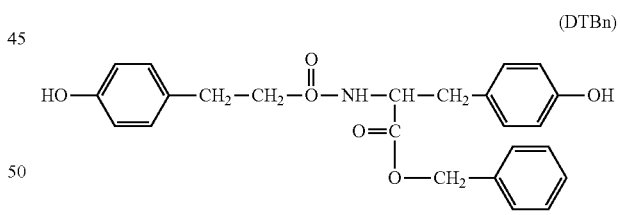

(DTBn)

were synthesized using the materials in Table 3.

TABLE 3

| Reagents | Amount (moles) |
| --- | --- |
| Tyrosine benzyl ester tosylate | 391.3 g (0.8823) |
| DAT | 43.4 g (0.8632) |
| Hydroxybenzotriazole hydrate (HOBT•H$_2$O) | 10.96 g (0.088) |
| Triethylamine | 123.3 ml (0.884 |
| N-methylpyrrolidinone (NMP) | 392 ml |
| EDCL•HCl | 172.17 g (0.8983) |
| Ethyl acetate (EtAc) | 978 ml + 1956 ml |
| Methylene chloride | >4 liters |
| Sodium bicarbonate | 0.5M |
| HCl | 0.2M |

TABLE 3-continued

| Reagents | Amount (moles) |
| --- | --- |
| Anhydrous magnesium sulfate | 30 g |
| Hexane | 1 liter |

The tyrosine benzyl ester tosylate (TBn-Tos) has the formula:

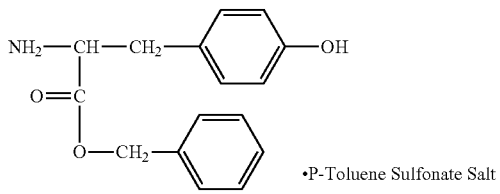 [SMILES: NC(Cc1ccc(O)cc1)C(=O)OCc1ccccc1]

•P-Toluene Sulfonate Salt

DAT has the formula:

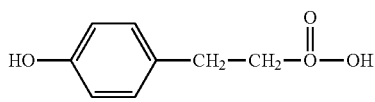

To synthesize DTBn, DAT, TBn-Tos and HOBT were added to 250 ml of the NMP in a 5 liter 3-necked flask and were stirred with a mechanical stirrer until a smooth slurry was obtained (15-30 minutes). 900 mL of EtAc was added and stirred for 15 minutes. The flask was cooled using an ice-water bath and was stirred for about 20 minutes in the cold (5° C.). Triethylamine was added. EDCI was added in one portion to the stirred reaction mixture and was washed down with the remaining Ethyl Acetate. The flask was capped and stirred for 4 h and the temperature was allowed to reach room temperature (25° C.) in the ice-bath without replenishing the melting ice. The reaction was stirred overnight. 1956 ml of Ethyl Acetate was added and stirred for 1 hour. The entire reaction mixture was transferred to a 22 L separatory funnel already containing 2000 ml of distilled water. The funnel contents were stirred with an overhead mixer to afford homogeneity. After layer separation was been achieved, the lower aqueous layer was drawn off and discarded. The ethyl acetate solution was extracted with the following reagents in the order indicated:
3×500 ml of 0.5M sodium bicarbonate:
1×500 ml of 20% sodium chloride.
3×500 ml of 0.2 M HCl
1×500 ml of 20% sodium chloride.

The upper ethyl acetate layer was drawn off and 30 g of anhydrous magnesium sulfate was added and stirred for 30 minutes. The mixture was allowed to stand in the covered flask at least 1-2 h. The mixture was then filtered. The filtrate was concentrated by vacuum distillation (rotovap) to a thick but mobile liquid without letting the temperature of the solution exceed 45° C. The thick liquid was poured into a 3 L resin kettle and was seeded with 50-100 mg of certified DTBn. After the product crystallizes, 1 L of hexane was added and stirred for 4 hours. The solid was then filtered. The solid was washed with 2× stationary overflow portions of hexane. The solid was dried under vacuum <1 mmHg for 20 h (max temp 50° C.). The yield of DTBn was 400 g (80%).

In Examples 1-3, all reagents used were ACS grade or better. Incoming materials were accepted based on COA and ID testing. Vendors for the reagents may include Fisher, VWR, Sigma Aldrich and Spectrum.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for preparing diphenol compounds having the formula:

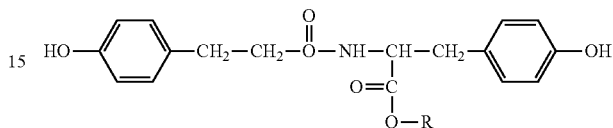

the method comprising:
adding a hydroxyphenyl carboxylic acid having the formula:

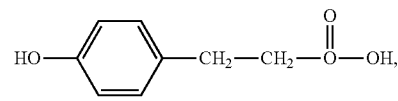

a tyrosine alkyl ester having the formula:

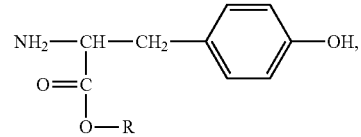

hydroxybenzotriazole hydrate and a solvent to a flask and stirring the contents of the flask to produce a first solution;
adding 3-ethyliminomethyleneamino-N,N dimethlpropan-1-amine (EDCI) HCl to the first solution to produce a first mixture;
adding ethyl acetate to the first mixture to produce a second mixture;
adding the second mixture to sodium chloride to produce a third mixture having layer separation;
removing an aqueous layer from the third mixture;
extracting the third mixture with reagents after the aqueous layer has been removed from the third mixture to produce a fourth mixture;
adding magnesium sulfate to the fourth mixture to produce a fifth mixture;
filtering the fifth mixture to produce filtrate;
concentrating the filtrate;
inducing crystallization of the concentrated filtrate; and
adding methylene chloride to the crystallized filtrate to produce a solid product,
wherein R is selected from a group consisting of alkyl groups having between 1 and 10 carbon atoms, alkyl groups having between 10 and 20 carbon atoms, and alkyl groups having more than 20 carbon atoms, and
wherein the tyrosine ethyl ester is added to the flask and the hydroxyphenyl carboxylic acid is metered into the flask after the tyrosine ethyl ester is added to the flask.

2. A method as recited in claim 1, wherein R is an ethyl group.

3. A method as recited in claim 1, wherein the solvent is selected from the group consisting of N-methylpyrollidone (NMP), tetrahydrofuran (THF), and methylene chloride.

4. A method as recited in claim 1, wherein the ethyl acetate is added as a cosolvent.

5. A method as recited in claim 1, wherein the first solution comprises at least about 2% excess of the tyrosine ethyl ester relative to the hydroxyphenyl carboxylic acid.

6. A method as recited in claim 1, wherein the first solution, the mixtures, the filtrate and the solid product are maintained at about 5° C. to about 10° C.

7. A method as recited in claim 1, wherein concentrated filtrate is crystallized by adding a 10:3 mixture of methylene chloride and toluene.

8. A method as recited in claim 1, wherein the method is complete after about 1 hour to about 2 hours.

9. A method as recited in claim 1, wherein the method is complete in less than 2 hours.

10. A method for preparing diphenol compounds having the formula:

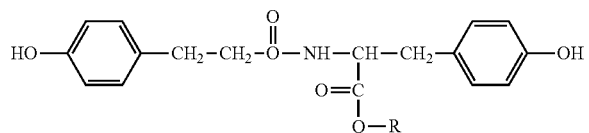

the method comprising:
adding a hydroxyphenyl carboxylic acid having the formula:

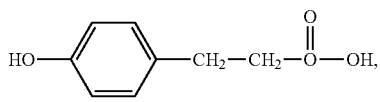

a tyrosine alkyl ester having the formula:

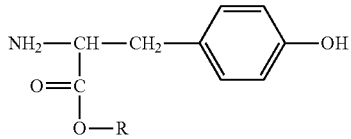

hydroxybenzotriazole hydrate and a solvent to a flask and stirring the contents of the flask to produce a first solution;
adding 3-ethyliminomethyleneamino-N,N dimethlpropan-1-amine (EDCI) HCl to the first solution to produce a first mixture;
adding ethyl acetate to the first mixture to produce a second mixture;
adding the second mixture to sodium chloride to produce a third mixture having layer separation;
removing an aqueous layer from the third mixture;
extracting the third mixture with reagents after the aqueous layer has been removed from the third mixture to produce a fourth mixture;
adding magnesium sulfate to the fourth mixture to produce a fifth mixture;
filtering the fifth mixture to produce filtrate;
concentrating the filtrate; and
adding methylene chloride to the concentrated filtrate to produce a solid product,
wherein R is selected from a group consisting of alkyl groups having between 1 and 10 carbon atoms, alkyl groups having between 10 and 20 carbon atoms, and alkyl groups having more than 20 carbon atoms, and
wherein the tyrosine ethyl ester is added to the flask and the hydroxyphenyl carboxylic acid is metered into the flask after the tyrosine ethyl ester is added to the flask.

11. A method as recited in claim 10, wherein R is an ethyl group and the concentrated filtrate is not crystallized.

12. A method for preparing diphenol compounds having the formula:

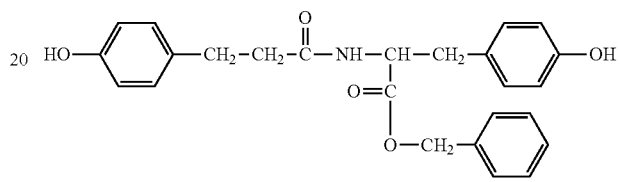

the method comprising:
adding a hydroxyphenyl carboxylic acid having the formula:

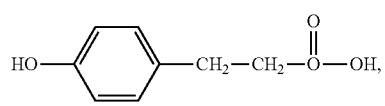

a tyrosine benzyl ester having the formula:

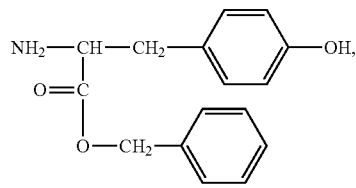 [SMILES: NC(Cc1ccc(O)cc1)C(=O)OCc1ccccc1]

hydroxybenzotriazole hydrate and a solvent to a flask and stirring the contents of the flask to produce a first mixture;
adding triethylamine to the first mixture to produce a second mixture;
adding EDCI HCl to the second mixture to produce a third mixture;
adding ethyl acetate to the third mixture to produce a fourth mixture;
adding the fourth mixture to distilled water to produce a fifth mixture having layer separation;
removing an aqueous layer from the fifth mixture;
extracting the fifth mixture with reagents after the aqueous layer has been removed from the fifth mixture to produce a sixth mixture;
adding magnesium sulfate to the sixth mixture to produce a seventh mixture;
filtering the seventh mixture to produce filtrate;
concentrating the filtrate;
inducing crystallization of the concentrated filtrate; and adding hexane to the crystallized filtrate to produce a solid product;

wherein the tyrosine ethyl ester is added to the flask and the hydroxyphenyl carboxylic acid is metered into the flask after the tyrosine ethyl ester is added to the flask.

13. A method as recited in claim 12, wherein the solvent is tetrahydrofuran (THF).

14. A method as recited in claim 12, wherein the solvent is a chlorinated solvent.

15. A method as recited in claim 12, wherein the mixtures, the filtrate and the solid product are maintained at about 5° C. to about 10° C. at all times during the method.

16. A method as recited in claim 12, further comprising stirring the first mixture for about 15 minutes to about 30 minutes.

17. A method as recited in claim 16, wherein the mixtures, the filtrate and the solid product are maintained at about 5° C. to about 10° C.

18. A method as recited in claim 12, wherein the method is complete after about 1 hour to about 2 hours.

19. A method as recited in claim 12, wherein the method is complete in less than 2 hours.

20. A method as recited in claim 1, wherein the reaction time for the metering is about 2 hours.

* * * * *